(12) United States Patent
Jabbari

(10) Patent No.: US 9,101,654 B2
(45) Date of Patent: Aug. 11, 2015

(54) BIORESORBABLE COMPOSITE FOR REPAIRING SKELETAL TISSUE

(75) Inventor: Esmaiel Jabbari, Columbia, SC (US)

(73) Assignee: University of South Carolina, Columbia, SC (US)

( * ) Notice: Subject to any disclaimer, the term of this patent is extended or adjusted under 35 U.S.C. 154(b) by 1657 days.

(21) Appl. No.: 11/995,612

(22) PCT Filed: Jul. 12, 2006

(86) PCT No.: PCT/US2006/026948
§ 371 (c)(1),
(2), (4) Date: Aug. 1, 2008

(87) PCT Pub. No.: WO2007/008927
PCT Pub. Date: Jan. 18, 2007

(65) Prior Publication Data
US 2009/0110732 A1    Apr. 30, 2009

Related U.S. Application Data

(60) Provisional application No. 60/741,010, filed on Nov. 30, 2005, provisional application No. 60/698,307, filed on Jul. 12, 2005, provisional application No. 60/741,002, filed on Nov. 30, 2005.

(51) Int. Cl.
*A61K 31/765* (2006.01)
*A61L 27/36* (2006.01)
*C08L 67/04* (2006.01)
*A61L 27/18* (2006.01)

(52) U.S. Cl.
CPC .............. *A61K 31/765* (2013.01); *A61L 27/18* (2013.01); *A61L 27/365* (2013.01); *C08L 67/04* (2013.01)

(58) Field of Classification Search
None
See application file for complete search history.

(56) References Cited

U.S. PATENT DOCUMENTS

| | | | |
|---|---|---|---|
| 5,512,653 A * | 4/1996 | Ohta et al. | 528/361 |
| 6,221,397 B1 | 4/2001 | Russell-Jones et al. | |
| 6,696,073 B2 | 2/2004 | Boyce et al. | |
| 2002/0028189 A1* | 3/2002 | Jo et al. | 424/78.3 |
| 2003/0180344 A1 | 9/2003 | Wise et al. | |
| 2004/0023028 A1* | 2/2004 | Yaszemski et al. | 428/402 |
| 2004/0024081 A1* | 2/2004 | Trieu et al. | 523/113 |
| 2005/0124720 A1* | 6/2005 | Rizzoli et al. | 523/115 |

FOREIGN PATENT DOCUMENTS

WO    WO 2005/002596    *    1/2005    .............. A61K 31/74

OTHER PUBLICATIONS

Chung et al., Sol-Gel Transition Temperature of PLGA-g-PEG Aqueous Solutions, Biomacromolecules 2002, 3, 511-516.*
Kato et al., Rate-limiting steps in volume change kinetics of fast responsive microporous gels, Chap. 8, Reflexive Polymers and Hydrogels.*
International Search Report and Written Opinion for PCT Application No. PCT/US2006/26948, Completed Dec. 27, 2006.

* cited by examiner

*Primary Examiner* — Kevin S Orwig
(74) *Attorney, Agent, or Firm* — Dority & Manning, P.A.

(57) ABSTRACT

Bioresorbable compositions for treating skeletal tissue are disclosed. The biomedical compositions are formed from a polylactide polymer, a polyglycolide polymer, or a poly(lactic-co-glycolic acid) polymer having a relatively low molecular weight. For instance, the average number molecular weight of the polymer is generally less than 10,000, such as from about 500 to about 5,000. Fumarate groups are incorporated into the low molecular weight polymer that provide crosslinking sites. If desired, ethyl-lene oxide groups and ceramic particles may also be incorporated into the polymer for producing compositions having a variety of properties. For example, the biomedical composition of the present disclosure can be used to treat soft skeletal tissue or to treat hard skeletal tissue. The biomedical compositions are biodegradable and can contain various therapeutic, beneficial and pharmaceutical agents that may be released during degradation of the polymer.

13 Claims, 6 Drawing Sheets

BIORESORBABLE COMPOSITE FOR REPAIRING SKELETAL TISSUE

RELATED APPLICATIONS

The present application is based upon and claims priority to U.S. Provisional Application Ser. No. 60/698,307 filed on Jul. 12, 2005, U.S. Provisional Application Ser. No. 60/741,010 filed on Nov. 30, 2005 and U.S. Provisional Application Ser. No. 60/741,002 also filed on Nov. 30, 2005.

BACKGROUND OF THE INVENTION

There are about 6.3 million fractures in the United States annually and closed fractures constitute a vast majority of these fractures. There are roughly 1,000,000 patients who have skeletal defects each year in the United States that require bone graft procedures to achieve union. These include applications arising from resection of primary and metastatic tumors, bone loss after skeletal trauma, primary and revision total joint arthroplasty with bone deficiency, spinal arthrodesis, and trabecular voids following osteoporotic insufficiency fractures. Bone grafts are also required to fill voids in metaphyseal bone fractures which include the distal radius, tibial plateau, proximal femur, and calcaneous fractures. Bone grafts are also used in other orthopedic applications such as being used as a bone fixative, as a suture reinforcement, and as scaffolds for guided regeneration of the alveolar bone in dentistry and reconstruction of mandibula, femoral neck osteonecrosis, and fusion of spinal processes.

Current clinical methods of treating skeletal defects involve bone transplantation or the use of other materials to restore continuity. Autologous bone graft has generally been the preferred bone replacement method because it provides osteogenic cells, osteoinductive factors, and an osteoconductive matrix for healing. However, the limited supply of autograft bone and donor site morbidity both restrict its use.

Allograft bone, although available in abundant supply, has drawbacks that include reduced rates of graft incorporation compared to autograft bone, and the possibility of pathogen transfer from donor to host.

Metals provide immediate mechanical support at the defect site but exhibit less than ideal overall integration with host tissue and can eventually fail due to fatigue loading if the bone does not heal prior to fatigue failure of the metal.

Ceramics, such as β-tricalcium phosphate (β-TCP) and hydroxyapatite (HA) are both osteoconductive, and have found clinical use as surface coatings on metal prostheses to enhance bonding to bone. In particulate form, they offer increased mechanical strength to polymeric composite materials primarily in compression, but are less effective in enhancing resistance to torsional and bending forces.

Polymethyl methacrylate (PMMA) bone cement can be injected or molded and is sometimes used to fill both cavitary and segmental defects, such as those that result from the curettage of a giant cell tumor or from the resection of a vertebral body in metastatic disease, respectively. However, the bone cement undergoes an exothermic polymerization reaction during implantation and can release a substantial amount of heat that risks local tissue injury. Additionally, PMMA is non-biodegradable and can thus accumulate fatigue damage with time and eventually undergo mechanical failure.

The use of polyhyroxyalkanonates such as homopolymers of poly(L-lactic acid) (PLLA), poly(glycolic acid) (PGA), polycaprolactone (PCL), poly(trimethylene carbonate), poly(butylene terephthalate), poly(hydroxybutyrate), poly(hydroxyvalerate), and poly(dioxanone) (PDS) and their copolymers is limited to rigid preformed devices. A group of photopolymerizable poly(anhydrides) consisting of polymers of sebacic acid (SA) alone, or copolymers of SA with either 1,3-bis(p-carboxyphenoxy) propane, or 1,6-bis(p-carboxyphenoxy) hexane (CPH) have been developed for orthopedic applications as scaffolds but ultraviolet light is typically required in the crosslinking step which can limit their use to shallow skeletal defects.

Poly(propylene fumarate) polymers have been developed for orthopedic applications but their degradation rate is very slow taking more than a year to degrade. Poly(caprolactone fumarate) polymers have also been developed to improve degradibility and injectibility compared to poly(propylene fumarate). However, poly(caprolactone) has significantly lower mechanical strength in compression compared to poly(propylene fumarate).

In addition to hard skeletal tissue fractures and defects, many people also suffer from soft skeletal tissue injuries, such as injuries or defects to cartilage. For instance, an estimated 43 million Americans are affected by arthritis, a condition associated with degeneration of the involved joint surfaces, and one million patients every year undergo surgery for osteoarthritis of their knees, hips, shoulders and spine. In addition to joint space narrowing, the degenerative articular cartilage changes often are associated with peripheral joint osteophytosis, subchondral bone sclerosis, and cystic bony changes.

Cartilage provides a smooth, near frictionless articulating surface and acts as a mediator for load transfer to the underlying subchondral bone. The regenerative capacity of damaged articular cartilage is limited compared with other musculoskeletal tissues such as bone and muscle. Mature articular cartilage has a limited potential for the repair of critical-sized defects because of its avascularity and the absence of stem cells. Cartilage defects can be due to traumatic injury, congenital abnormality, degenerative diseases (osteoarthritis) or can be age related.

Methods of treatment used for cartilage defects in the last three decades include lavage and debridement, penetration of the subchondral bone by arthroscopic abrasion, drilling, or microfracture techniques, altering joint loading, perichondrial or periosteal transplants, chondrocyte or mesenchymal stem cell transplant, treatment with growth factors, mechanical loading, joint osteotomy, and total joint replacement. There are many disadvantages of these procedures. These procedures show only temporary positive outcomes, can cause donor site morbidity, involve pathogen transfer for allograft procedures, show reduced biological activity in the grafts for elderly patients, have unfavorable long-term clinical outcomes, and are highly invasive. Furthermore, the success of the treatment depends on the severity of injury and age of the patient. Small defects heal more quickly than larger defects and articular injuries heal more quickly in children than in adults.

In view of the above, a need currently exists for biomedical compositions and methods of repairing skeletal tissue. In particular, a need currently exists for a biomedical composition that may be used for skeletal tissue support and/or regeneration that cannot only be used to treat hard skeletal tissue but also can be used to treat soft skeletal tissue.

In this regard, the present disclosure is directed to biomedical compositions that, once crosslinked, provide a polymer network for use in treating skeletal tissue. Of particular advantage, the biomedical compositions can be formulated and tailored for treating hard skeletal tissue and/or soft skeletal tissue. In one embodiment, for instance, the present disclosure is directed to a biodegradable scaffold composition that comprises a hydrogel/ceramic nanocomposite that can provide temporary structural support to regenerating skeletal tissue and can degrade concurrently with the migration of bone marrow stromal cells.

In an alternative embodiment, the present disclosure is directed to a biomedical hydrogel composition particularly well suited for treating soft skeletal tissue. Of particular advantage, the hydrogel composition can be injected and hardened in-situ. Once applied, the hydrogel composition can form a matrix that can guide the organization, differentiation, proliferation and development of seeded cells into the desired tissue.

SUMMARY OF THE INVENTION

In general, the present disclosure is directed to biomedical compositions that are particularly well suited for treating skeletal tissue. For example, the compositions can be used as a scaffold for skeletal tissue regeneration that, once implanted, biodegrade over a desired period of time.

In one embodiment, for instance, the present disclosure is directed to a bioresorbable and crosslinkable composition for biomedical applications. The composition comprises a fumaryl compound reacted with a biodegradable polymer. The biodegradable polymer may comprise a polylactide polymer, a polyglycolide polymer, or a poly(lactic-co-glycolic acid) copolymer. In accordance with the present disclosure, the biodegradable polymer has a relatively low molecular weight. For instance, the biodegradable polymer can have an average number molecular weight of less than about 5,000 Daltons, such as from about 1,000 Daltons to about 4,000 Daltons or from about 1,000 Daltons to about 3,000 Daltons. The biodegradable polymer can also have a polydispersity index of less than about 3, such as less than about 2.5, such as less than about 2, such as less than about 1.8.

The fumaryl compound forms unsaturated reactive groups on the resulting biodegradable polymer. In general, fumaric acid or any suitable fumaryl compound may be used. For instance, in one embodiment, the fumaryl compound may comprise fumaryl chloride. In forming the polymer, the molar ratio of the biodegradable polymer to the fumaryl compound can be from about 1:0.8 to about 1:0.99.

Once the fumaryl compound is reacted with the biodegradable polymer, the biodegradable polymer may comprise, depending upon the initial monomer, poly(lactide fumarate), poly(glycolide fumarate), or poly(lactide-co-glycolide fumarate). The resulting polymer may have a number average molecular weight of less than about 10,000 Daltons, such as less than about 6,500 Daltons.

In one embodiment, in order to form a hydrogel composition that is particularly well suited for treating soft skeletal tissue, the fumaryl compound and the biodegradable polymer may also be reacted with an ethylene oxide-based Compound. The ethylene oxide compound can form ethylene oxide groups in the resulting polymer. More particularly, a hydrophilic polymer comprising poly(lactide-ethylene oxide-fumarate) may be formed.

When forming the hydrophilic polymer, the molar ratio of the fumaryl compound to the biodegradable polymer and the ethylene oxide compound can be from about 0.8:1 to about 0.99:1. The ethylene oxide compound may comprise, for instance, a polyethylene glycol, including diethylene glycol. The weight ratio of the ethylene oxide compound to the biodegradable polymer may be from about 99:1 to about 50:50.

In still another embodiment, the above described hydrophilic polymer may be crosslinked in the presence of ceramic nanoparticles to form a composite polymer that is particularly well suited for treating hard skeletal tissue. The ceramic nanoparticles, for instance, may comprise calcium particles, such as a calcium phosphate. For instance, the nanoparticles may comprise an apatite or a tricalcium phosphate. The hydrophilic polymer may be crosslinked using any suitable crosslinking agent. For instance, in one embodiment, a peptide crosslinking agent may be used that is metalloproteinase degradable. Alternatively, the crosslinking agent may comprise methylene bis acrylamide.

Any of the above described biomedical compositions can be combined with a crosslinking agent and applied to a prepared area of a patient's body. For instance, the biomedical compositions, after being combined with a crosslinking agent, may be applied to skeletal tissue for repairing the tissue. Once applied, crosslinking of the composition may occur in-situ.

In addition to a crosslinking agent, the biodegradable polymer may also be combined with various other additives and ingredients. For instance, in one embodiment, an initiator and/or an accelerator may be combined during the crosslinking process in order to control the rate of reaction. Further, in one embodiment, a porogen may be incorporated into the resulting composition. The porogen, for instance, may comprise a water soluble salt or a sugar or any powder compound that leaches out with water. For instance, in one embodiment, the porogen may comprise sodium chloride.

The particular crosslinking agent selected to crosslink the biodegradable polymer may depend upon various factors and the particular application for which the resulting composition is to be used. For example, in one embodiment, when the biomedical composition contains polyethylene oxide units, the crosslinking agent may comprise methylene bis acrylamide. When the biomedical composition contains ceramic particles, on the other hand, the crosslinking agent may comprise either methylene bis acrylamide or a peptide crosslinking agent, such as a peptide crosslinking agent that is metalloproteinase degradable.

As described above, the biomedical compositions are generally formed from a fumaryl compound reacted with a biodegradable polymer. The biodegradable polymer may be formed by melt ring opening polymerization of a monomer. The monomer may comprise, for instance, a lactide, a glycolide, or a lactide-glycolide.

After the melt ring opening polymerization process, the polymer can be purified by vacuum and/or by precipitation in multiple solvents. The solvents may include, for instance, methylene chloride, methanol, ethyl acetate, ether, and/or hexane.

When sold commercially to medical professionals, the biomedical composition can be sold as a two-part product. For example, the biomedical product may include a first container comprising a biodegradable polymer that includes poly(lactide fumarate), poly(glycolide fumarate) or poly(lactide-co-glycolide fumarate). The biomedical product may further include a second container that contains a crosslinking agent for the biodegradable polymer. In this manner, the contents of both containers can be combined and applied to skeletal tissue for crosslinking in-situ.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which:

FIG. 7 is a graphical representation of the results obtained in Example No. 3 below while

DETAILED DESCRIPTION

Figure 1:
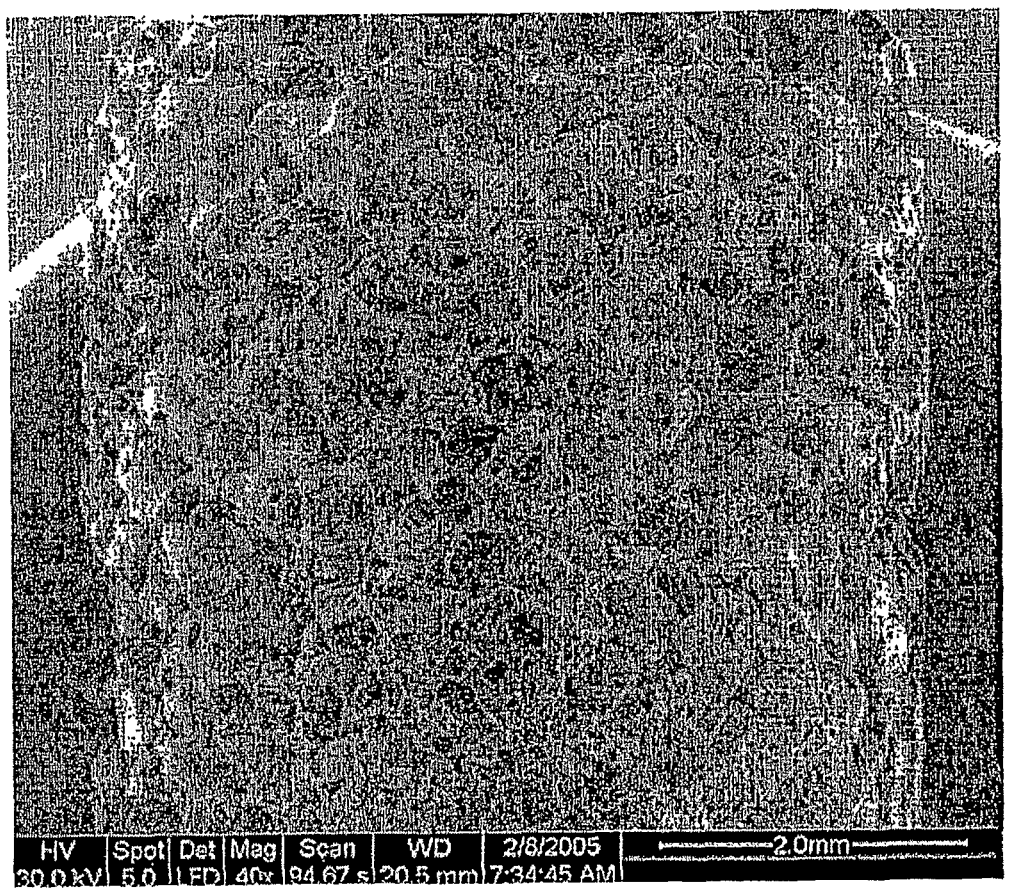
FIGS. 1 and 2 are pictures of one embodiment of a biomedical composition made in accordance with the present disclosure.

It is to be understood by one of ordinary skill in the art that the present discussion is a description of exemplary embodiments only, and is not intended as limiting the broader aspects of the present invention.

In general, the present disclosure is directed to biomedical compositions that are biodegradable and are particularly well suited for use in treating skeletal tissue. Of particular advantage, the biomedical compositions can be constructed having various properties. In particular, the biomedical composition can be tailored to a particular application. In this manner, the biomedical composition can be used to not only treat hard skeletal tissue, but can also be used to treat soft skeletal tissue, such as cartilage.

Also of advantage, the biomedical compositions can be formed so as to be completely bioresorbable. Thus, once implanted in the body, the biomedical compositions degrade over a period of time. Further, by altering the manner in which the biomedical composition is made, the length of time it takes for the composition to biodegrade can be controlled. In one particular embodiment, for instance, the biomedical composition can be used as a scaffold for skeletal tissue regeneration. Once implanted, the biomedical composition degrades as the skeletal tissue regenerates. In this manner, the biomedical composition provides temporary structural support to the reconstructed region and can also provide a medium for solubilization, diffusion, release of nutrients and growth factors, and their interactions with cells.

Another benefit to the biomedical compositions of the present disclosure is that the compositions, if desired, can be crosslinked in-situ during the treatment of skeletal tissue. In this manner, the compositions can be molded into shape during implantation. Thus, the compositions are well suited to accommodating any shape irregularities that may exist in the existing tissue structure that is being treated. For example, in one embodiment, the biomedical composition can be formed into a paste that conforms to the shape of irregular defects present at the treated site. Alternatively, the biomedical composition may be formed into a viscous liquid composition that is injected into the prepared area in a minimally invasive procedure. Once implanted, the composition can be configured to crosslink and form a structural scaffold for the skeletal tissue.

As will be discussed in greater detail below, the biomedical compositions of the present disclosure are generally formed from a relatively low molecular weight biodegradable polymers or macromers. The biodegradable polymer, for instance, may comprise a polylactide polymer, a polyglycolide polymer, or a poly(lactic-co-glycolic acid) copolymer. The biodegradable polymer is reacted with a fumaryl compound that incorporates fumarate groups into the polymer. The fumarate groups provide sites for crosslinking and in-situ hardening.

In one embodiment, ethylene oxide groups may be further incorporated into the biodegradable polymer. For example, a poly(lactide-ethylene oxide-fumarate) terpolymer may be formed or a poly(lactide-co-glycolide-ethylene oxide-fumarate) terpolymer may be formed. The ethylene oxide groups that are incorporated into the polymer are hydrophilic, thus creating a hydrogel polymer when crosslinked.

The biodegradabe polymer may be crosslinked with the aid of a synthetic or natural crosslinking agent and optionally an initiator and an accelerator.

In still another embodiment of the present disclosure, ceramic particles can be incorporated into the biodegradable polymer for providing a composition particularly well suited for treating hard skeletal tissue. For example, in one embodiment, ceramic nanoparticles can be incorporated into the above described biodegradable polymers. The ceramic particles may, for instance, comprise any suitable calcium compound, such as a calcium phosphate. Examples of calcium phosphates that may be used include apatite particles or tricalcium phosphate particles.

If desired, the ceramic particles can be incorporated into the biodegradable polymer as the polymer is crosslinked using any suitable crosslinking agent. For instance, the crosslinking agent, in one embodiment, may comprise a peptide crosslinking agent that is metalloproteinase degradable. The ceramic particles are incorporated into the biodegradable polymer in order to modulate the matrix degradation kinetics with the migration of bone marrow stromal cells. Such polymers are particularly well suited for being used as degradable scaffolds that are biocompatible and can support cell attachment and migration.

Biodegradable Polymers Formed From Relatively Low Molecular Weight Macromers

As described above, the biomedical compositions of the present disclosure are generally formed from relatively low molecular weight polylactide polymers, polyglycolide polymers, and/or poly(lactic-co-glycolic acid) copolymers. Of particular advantage, all of the above polymers are biodegradable. Polylactide, for instance, is a biodegradable, thermoplastic, aliphatic polyester derived from lactic acid. Lactic acid exists in L form and in D form. Polylactide formed from L-lactic acid produces a polymer having some crystallinity. For instance, the crystallinity of the polymer may be from about 25% to about 45%. The polymerization of a mixture of both L and D forms of lactic acid, on the other hand, creates a substantially amorphous polymer.

Polyglycolide polymers, on the other hand, are formed from glycolic acid. Glycolic acid is an alpha-hydroxy acid.

Poly(lactic-co-glycolic acid) is a copolymer formed from both glycolic acid and lactic acid. During polymerization, the monomer units are linked together by ester linkages thus yielding a linear, aliphatic polyester. When forming a biomedical composition according to the present disclosure from poly(lactic-co-glycolic acid), the ratio of lactide to glycolide in the resulting polymer can vary. For instance, the copolymer can contain lactide in a mole percentage of from about 1% to about 90%.

In the past, polylactides, polyglycolides, and poly(lactic-co-glycolic acid) copolymers have been used in various biomedical applications. In the past, however, the polymers were typically formed so as to have a relatively high molecular weight. For instance, commercially available poly(lactic-co-glycolic acid) copolymers typically have a molecular weight of greater than 15,000. In the present disclosure, on the other hand, relatively low molecular weight biodegradable polymers are used.

The biodegradable polymers can be formed, for instance, by melt ring opening polymerization of lactide, glycolide or lactide-glycolide monomers in bulk in the presence of an initiator and a catalyst. In general, relatively large amounts of an initiator are used in conjunction with a catalyst. After the reaction, the remaining monomer can be removed by vacuum. The relatively low molecular weight polymer is precipitated in ether, methanol, hexane or any other suitable solvent and purified. Ultimately, biodegradable polymers are obtained that have an average number molecular weight of generally greater than about 500 Daltons and generally less than about 8,000 Daltons. For instance, in one embodiment, the average number molecular weight can be from about 500 to about 5,000 Daltons.

Higher molecular weights are generally not desired. In particular, the present inventor has discovered that polylactide, polyglycolide or poly(lactic-co-glycolic acid) polymers having relatively high molecular weights generally do not provide acceptable crosslink densities thereby creating compositions that do not have suitable 3-dimensional stability.

The solvent that may be selected during the purification process may vary depending upon the particular application. Preferably, the relatively low molecular weight polymers are insoluble in the solvent as they precipitate so that the polymers may be easily separated and collected. Examples of solvents that may be used, for instance, include methylene chloride, methanol, ethyl acetate, ether, or hexane.

Similarly, the initiator and catalyst selected may also vary. In one embodiment, for instance, the initiator may comprise a glycol, such as diethylene glycol. The catalyst, on the other hand, may comprise tin, II-ethyl hexanoate, tin II-chloride, or a stannous octoate catalyst.

The molar ratio of initiator to catalyst may be useful in producing the relatively low molecular weight polymers. For instance, the molar ratio of initiator to catalyst may be from about 10:1 to about 50:1, such as from about 20:1 to about 30:1. In one particular embodiment, for instance, the molar ratio of initiator to catalyst may be about 25:1.

The molar ratio of monomer to initiator can also be varied in order to vary the molecular weight of the resulting polymer. The molar ratio of monomer to initiator, for instance, may be from about 50:1 to about 5:1, such as from about 30:1 to about 10:1. Decreasing the ratio of monomer to initiator can generally be used to decrease the average molecular weight of the resulting polymer.

The relatively low molecular weight biodegradable polymers can also be made so as to have a relatively low polydispersity index. For instance, the polydispersity index can generally be less than about 3, such as less than about 2. For instance, in one embodiment, the polydispersity index can be less than about 1.8, such as from about 1 to about 1.7.

The biodegradable polymers as formed above generally are terminated with a functional group. For instance, the polylactide polymer, the polyglycolide polymer, or the polylactic-co-glycolic acid) copolymer can be hydroxyl terminated. In addition to hydroxy groups, however, it should be understood that various other functional groups may be present in the terminal position. For instance, in an alternative embodiment, the biodegradable polymer may be terminated with amine groups.

Once the biodegradable polymer is formed, unsaturated reactive groups are incorporated into the polymer chains in order to create a polymer that is crosslinkable. For instance, in one embodiment, fumarate groups may be incorporated into the biodegradable polymer. Fumarate groups may be incorporated into the polymer by reacting the polymer with a fumaryl compound, such as a fumaryl chloride or fumaric acid.

For instance, in one particular embodiment, fumaryl chloride may be reacted with the biodegradable polymer in the presence of a catalyst and a solvent. In general, any suitable catalyst may be used such as triethylamine. The solvent may comprise methylene chloride. It should be understood, however, that any manner of incorporating fumarate groups into the biodegradable polymer may be used in accordance with the present disclosure.

In reacting the fumarate with the biodegradable polymer, the amount of fumarate groups incorporated in the polymer can be varied in order to control the properties of the resulting polymer. For instance, a greater amount of fumarate groups incorporated into the polymer will generally lead to a greater amount of crosslinking. Increasing the amount of crosslinking can decrease the degradation rate of the polymer. Thus, if it is desirable to increase the period of time over which the polymer will degrade once implanted, greater amounts of fumarate groups may be incorporated into the polymer. In general, the molar ratio of the biodegradable polymer to the fumaryl compound can be from about 1:0.8 to about 1:0.99, such as from about 1:0.85 to about 1:0.99. The molar ratio of the catalyst to the fumaryl compound can also vary and can generally be from about 1.5:1 to about 2.5:1, such as about 2:1.

Once the biodegradable polymer is reacted with the fumaryl compound, poly(lactide fumarate), poly(glycolide fumarate), or poly(lactide-co-glycolide fumarate) is produced. The resulting biodegradable polymer may continue to have an average molecular weight that is relatively low, such as less than about 15,000. For instance, the average molecular weight of the resulting biodegradable polymer may be less than about 12,000, such as from about 1,000 to about 10,000. The polydispersity index of the resulting polymer can be less than about 3, such as from about 1 to about 2.5.

The biodegradable polymer containing the fumarate groups can be in the form of a powder once formulated. When treating skeletal tissue, the biodegradable polymer can be combined with a crosslinking agent and applied to a prepared area of a patient's body for use in generating new skeletal tissue. In one embodiment, for instance, the biodegradable polymer can be formulated into a paste for the fabrication of a bone cement scaffold for in-situ orthopedic applications. For example, when the biodegradable polymer is combined with the crosslinking agent during a surgical procedure or operation, the composition can be molded into a particular shape and implanted in the patient or alternatively can be injected to fill skeletal defects or injuries for guided bone regeneration. In the above embodiments, crosslinking of the polymer continues to occur after the composition has been applied to the treated area.

Alternatively, the biodegradable polymer and the crosslinking agent can be combined together and molded into a particular shape until crosslinking discontinues. The resulting shaped product can then be implanted into a patient where desired.

The crosslinking agent that is combined with the biodegradable polymer can vary depending upon the particular application and the particular construction of the polymer. For instance, in one embodiment, the poly(lactide fumarate), poly(glycolide fumarate), or poly(lactide-co-glycolide fumarate) polymer may be combined with 1-vinyl-2-pyrrolidinone as the crosslinking agent. The crosslinking agent can be combined with the biodegradable polymer in the presence of a solvent, such as water, in order to ensure proper mixing of the two components. Other crosslinking agents that may be used include, for instance, acetic anhydride, ethylene glycol diacrylate, ethylene glycol dimethacrylate, or any other suitable compound containing unsaturated functional groups.

The amount of crosslinking agent combined with the biodegradable polymer can vary depending upon various factors including the particular crosslinking agent chosen, the amount of crosslinking that is desired, and the amount of fumarate groups that has been incorporated into the polymer. In general, the crosslinking agent can be present in an amount from about 5% to about 50% by weight of the polymer, such as from about 10% to about 30% by weight, such as from about 15% to about 25% by weight.

If desired, the crosslinking agent can be combined with the biodegradable polymer in the presence of other ingredients, such as an initiator and an accelerator. In general, any suitable free radical initiator and accelerator may be used. For example, any suitable initiator that dissolves in an organic solvent may be used. In one embodiment, for instance, benzoyl peroxide may be used as a free radical initiator, while dimethyltoluidine may be used as an accelerator. In other embodiments, the initiator may comprise any initiator in the same class as benzoyl peroxide, while the accelerator may comprise any accelerator from the same class as dimethyltoluidine. In general, the initiator can be present in an amount from about 0.01% to about 2% by weight of the polymer, while the accelerator may be present in an amount from about 0.001% to about 0.5% by weight. The above weight percentages, however, have been provided merely for exemplary purposes.

In addition to the above, various other ingredients may be optionally added during crosslinking of the biodegradable polymer. For instance, in one embodiment, a porogen may be present during the reaction. A porogen is a material that causes pores to form in the resulting crosslinked polymer. The porogen may comprise, for instance, an effervescent material or a water soluble salt. For instance, in one embodiment, sodium chloride may be used as a porogen. The porogen may be present in the crosslinked composition in an amount from about 5% to about 95% by volume.

In addition to a porogen, various other beneficial compounds may be added to the composition. For instance, various pharmaceuticals and medicaments can be added to the composition that may be released from the composition during biodegradation. In this manner, the beneficial agents may be released as the polymer degrades. In one embodiment, for instance, an antibiotic agent may be incorporated into the biodegradable polymer. The antibiotic agent may be present in order to reduce the chance of any infection. In one embodiment, for instance, gentamiocin may be incorporated into the biomedical composition.

In another embodiment, bone morphogenetic protein (BMP) may also be incorporated into the biomedical composition. Bone morphogenetic proteins are a group of growth factors known for their ability to induce the formation of bone and cartilage. When present, the bone morphogenetic proteins may increase the rate of bone formation.

When the biomedical composition as described above is to form a scaffold in-situ, the composition can be packaged in at least two different containers. For example, one container can contain one or more biodegradable polymers, namely poly(lactide fumarate), poly(glycolide fumarate) and/or poly(lactide-co-glycolide fumarate). A second container can contain a crosslinking agent that is to be mixed in the presence of water with the biodegradable polymer. One or both of the containers can further include an initiator, an accelerator, a porogen, or any other desired ingredients or components. During a surgical operation, the contents of the containers can be mixed in the presence of a solvent such as water in order to initiate crosslinking of the material. The material can then be applied to a prepared area of a patient's body in order to treat skeletal tissue.

Incorporating Hydrophilic Groups into the Biodegradable Polymer

In one embodiment, hydrophilic groups may be incorporated into the biodegradable polymer for increasing the hydrophilicity of the material. In fact, sufficient amounts of the hydrophilic groups may be incorporated into the polymer in order to form a hydrogel polymer. Hydrogels, due to their hydrophilicity and high water content, coupled with minimally invasive arthroscopic techniques are an attractive cell carrier for treating irregularly shaped defects with minimal tissue dissection and retraction. After injection and hardening in-situ, hydrogel polymers made according to the present disclosure can form 3-dimensional matrices that guide the organization, differentiation, proliferation, and development of seeded cells into the desired tissue. Such hydrogel polymers are particularly well suited for treating soft skeletal tissue, such as cartilage. As described below, according to the present disclosure, terpolymer hydrogels can be constructed from the above described biodegradable polymers with controlled degradation, resorption, and in-situ crosslinking ability making them useful for a wide variety of applications and soft tissue regeneration.

In one embodiment, for instance, ethylene oxide groups can be incorporated into the biodegradable polymer. Thus, various poly(lactide-ethylene oxide-fumarate) polymers, poly(glycolide-ethylene oxide-fumarate) polymers and poly(lactide-co-glycolide-ethylene oxide-fumarate) polymers may be produced. The polylactide, polyglycolide, or poly(lactide-co-glycolide) blocks provide hydrophobicity to control the water content and provide sites for degradability. The poly(ethylene oxide) blocks provide hydrophilicity and the ability of the terpolymer to swell in aqueous physiologic medium. The fumarate groups, on the other hand, provide sites for crosslinking and in-situ hardening.

In order to form the hydrogel polymer and to incorporate the ethylene oxide groups into the polymer, a biodegradable polymer, such as polylactide, polyglycolide, or poly(lactic-co-glycolic) copolymer is first formed as described above having a relatively low molecular weight and polydispersity index. The biodegradable polymer is then combined with an ethylene oxide compound and a fumaryl compound and reacted together through condensation polymerization. The reaction can occur in the presence of a solvent and a catalyst. For instance, in one embodiment, the ethylene oxide compound and the biodegradable polymer are dissolved in methylene chloride and then combined with a fumaryl compound and a catalyst. Any suitable catalyst can be used, such as triethylamine.

The fumaryl compound can be any fumaryl compound as described above, such as fumaryl chloride. The ethylene oxide compound, on the other hand, can be any suitable compound capable of producing ethylene oxide groups within the polymer chain. In one embodiment, for instance, polyethylene glycol may be used. The polyethylene glycol may have a number average molecular weight of from about 500 Daltons to about 5,000 Daltons, such as from about 1,000 Daltons to about 3,500 Daltons.

The relative amounts of the reactants can be used to produce a product having desired characteristics and properties.

For instance, the relative amounts of reactants can be varied in order to vary the molecular weight, the hydrophilicity and hydrophobicity of the resulting polymer, the viscosity of the polymer, and the degradation characteristics of the polymer.

For example, the molar ratio of the fumaryl compound to the biodegradable polymer and the ethylene oxide compound can be from about 0.3:1 to about 1:1, such as from about 0.8:1 to about 0.95:1. The molar ratio of the catalyst to the biodegradable polymer and the ethylene oxide compound, on the other hand, can be from about 1:1 to about 2.5:1, such as about 1.8:1. The weight ratio of the ethylene oxide compound to the biodegradable polymer can also vary significantly. For instance, the weight ratio can vary from about 99:1 to about 1:99. In general, however, greater amounts of the ethylene oxide compound may be present in order to provide sufficient hydrophilicity. For instance, the weight ratio of the ethylene oxide compound to the biodegradable polymer can be from about 99:1 to about 50:50, such as from about 99:1 to about 70:30. In one particular embodiment, the weight ratio of the ethylene oxide compound to the biodegradable polymer can be about 85:15.

The resulting biodegradable polymer, which may be poly(lactide-ethylene oxide-fumarate), poly(glycolide-ethylene oxide-fumarate), or poly(lactide-co-glycolide-ethylene oxide-fumarate), may have a resulting number average molecular weight of less than about 15,000 Daltons, such as from about 500 Daltons to about 8,000 Daltons. The resulting biodegradable polymer may also have a polydispersity index of less than about 3.5, such as from about 1 to about 3. In one embodiment, for instance, the polydispersity index can be less than about 2.

When the biodegradable polymer containing the ethylene oxide groups and the fumarate groups is used for repairing skeletal tissue, such as soft skeletal tissue, the polymer can be combined with a crosslinking agent, an initiator, and an accelerator. In general, any suitable mono or multifunctional synthetic or natural crosslinking agent may be used. Also, any suitable initiator and accelerator may also be present. In one embodiment, for instance, the crosslinking agent may comprise methylene bis acrylamide. The initiator and accelerator may form a redox initiation system containing a reducing agent and an oxidizing agent. For instance, in one embodiment, a redox initiation system may be used containing ammonium persulfate in combination with tetramethylethylenediamine. The different components as described above may be mixed together in the presence of a solvent, such as water, and applied to skeletal tissue for treating the tissue. For instance, in one embodiment, the resulting mixture can be injected for in-situ crosslinking.

Not only is the resulting biodegradable hydrogel polymer particularly well suited for soft skeletal tissue regeneration, the composition is also well suited as a carrier for delivery of differentiated tissue cells, marrow stromal stem cells, or undifferentiated multipotent adult progenitor stem cells to skeletal tissue, especially cartilage defects. The degradation characteristics and injectibility of the hydrogel polymer can be tailored to different applications by using different ratios of the fumarate to lactide/glycolide and ethylene oxide groups. Further, the mechanical strength and in-situ crosslinkablility of the polymer network can be tailored to different applications by the density of fumarate groups and the extent of crosslinking.

Biodegradable Composite Polymers

In still another embodiment of the present disclosure, any of the above described biodegradable polymers may be combined with ceramic particles in order to produce a biomedical composition particularly well suited for treating hard skeletal tissue.

In general, in order to form a composite polymer, in this embodiment, a crosslinkable and biodegradable polymer is produced containing polylactide units, polyglycolide units, and/or poly(lactide-co-glycolide) units, fumarate units, and optionally polyethylene oxide units. The crosslinkable polymer is then combined with ceramic particles in the presence of a crosslinking agent to form the resulting composite polymer. The crosslinkable polymer may be any of the polymers described above that are made from a biodegradable polymer having a relatively low molecular weight and a relatively low polydisperity index.

The ceramic particles, in one embodiment, can comprise particles containing a calcium compound that are compatible with skeletal tissue. The ceramic particles, for instance, may comprise a calcium phosphate, such as apatite particles or tricalcium phosphate particles.

The ceramic particles generally have a relatively small particle size, such as an average particle size of less than about 1 micron. For instance, in one embodiment, the particles can have an average particle size of from about 10 nanometers to about 200 nanometers.

The amount of ceramic particles incorporated into the resulting composite polymer can vary depending upon the particular application and the structural rigidity that is needed. In general, for instance, the ceramic particles may be incorporated into the polymer in an amount from about 5% to about 40% by weight.

The ceramic particles are incorporated into the polymer matrix with the aid of a mono or multifunctional synthetic or natural crosslinking agent. For instance, in one embodiment, the crosslinking agent may comprise methylene bis acrylamide.

Alternatively or in addition to the above crosslinking agent, a peptide crosslinking agent may also be used. The peptide crosslinking agent can be constructed from any suitable amino acid sequence that is capable of crosslinking the fumarate groups to form the polymer matrix. Preferably, the peptide crosslinking agent is also metalloproteinase degradable. In one embodiment, for instance, the peptide crosslinking agent comprises lysine-alanine-isoleucine-glycine-glutamine-histidine-lysine amino acid sequence with unsaturated reactive end groups. For instance, the peptide crosslinking agent may contain unsaturated acrylate end groups by coupling acrylic acid to the amino acid end groups. It should be understood, however, that any suitable functional group may be added to the ends of the peptide crosslinking agent.

The crosslinking agent may be combined with the ceramic particles and the crosslinkable biodegradable polymer in the presence of water and in the presence of an initiator and/or an accelerator. The initiator may comprise, for instance, ammonium persulfate, while the accelerator may comprise tetramethylethylenediamine to form a redox initiation system.

In one embodiment, the crosslinkable polymer that is combined with the crosslinking agent and the ceramic particles comprises a hydrophilic polymer as described above containing ethylene oxide groups. For instance, the crosslinkable polymer may comprise poly(lactide-ethylene oxide-fumarate), poly(glycolide-ethylene oxide-fumarate), or poly(lactide-co-glycolide-ethylene oxide-fumarate), which forms a gel phase during the crosslinking reaction. By incorporating ethylene oxide groups into the polymer, an aqueous-based scaffold can be constructed. In particular, the water content of the resulting polymer can be adjusted by changing the ratio of the hydrophobic groups to the hydrophilic groups. The gel phase and the ceramic phase are crosslinked to modulate the matrix degradation kinetics with the migration of bone marrow stromal cells. The resulting composition has also been found to support cell attachment and migration.

The present disclosure may be better understood with reference to the following examples.

Example 1

In this example, polylactide, polyglycolide, and polylactic-co-glycolic acid) polymers were synthesized, reacted with a fumaryl compound, and crosslinked to produce a biomedical composition in accordance with the present disclosure.

In the first step, short hydroxyl-terminated polylactide, polyglycolide, or poly(lactic-co-glycolic acid) chains were synthesized by melt ring-opening polymerization of the lactide, glycolide, or lactide-glycolide monomer with diethylene glycol as the initiator and tin II-ethyl hexanoate as the reaction catalyst.

The molar ratio of initiator to catalyst was 25. The molar ratio of monomer to initiator was varied from 30 to 10. The polymer was purified by vacuum. Then the polymer was precipitated in multiple solvents including methanol, ether, and hexane.

The synthesized polylactide, polyglycolide, or poly(lactic-co-glycolic acid) was characterized by variety of chemical analysis techniques including 1H-NMR, FTIR, and gel permeation chromatography (GPC). When the ratio of lactide monomer to intiator was varied from 30 to 20 to 10, the number average molecular weight of the produced polylactide decreased from 6800 to 2600 to 1000 Dalton, respectively, and the polydispersity index increased from 1.3 to 1.7 to 2.0, respectively. When lactide and glycolide monomer with 50/50 weight ratio and monomer to intiator ratio 20 was used, a short chain poly(lactic-co-glycolic acid) polymer with number average molecular weight of 3500 Dalton and polydispersity index of 1.9 was produced.

In the second step, unsaturated reactive groups were added to the short polymer chains for in-situ crosslinkability, the polylactide, polyglyolide, or poly(lactic-co-glycolic acid) macromers were reacted with fumaryl chloride to produce poly(lactide fumarate), poly(glycolide fumarate), or poly (lactide-co-glycolide fumarate) macromers. Triethylamine (TEA) was used as the catalyst and the reaction was carried out in methylene chloride as the solvent. The molar ratio of polylactide, polyglycolide, or poly(lactic-co-glycolic acid) to fumaryl chloride was varied from 0.85 to 0.99. The molar ratio of TEA to fumaryl chloride was 2.

The produced unsaturated macromer was characterized by variety of chemical and physical characterization techniques including 1H-NMR, $^{13}$C-NMR, FTIR, GPC, and differential scanning calorimetry (DSC). Molecular weight of poly(lactide fumarate) depended on that polylactide used in the synthesis. The Mn of poly(lactide fumarate) increased from 4000 to 5200 Dalton as that of polylactide increased from 1000 to 2300. The polydispersity index of poly(lactide fumarate) (2.5) was significantly higher than that of polylactide (1.6) for all molecular weights. Copolymerization with Fumaric acid did not significantly affect the degree of crystallinity of polylactide, as measured by wide angle x-ray scattering and DSC. The melting point of the semi-crystalline poly(lactide-co-glycolide fumarate), measured by DSC, depended on the molecular weight and fraction of glycolide in the synthesized low molecular weight poly(lactic-co-glycolic acid) polymer.

Figure 2:
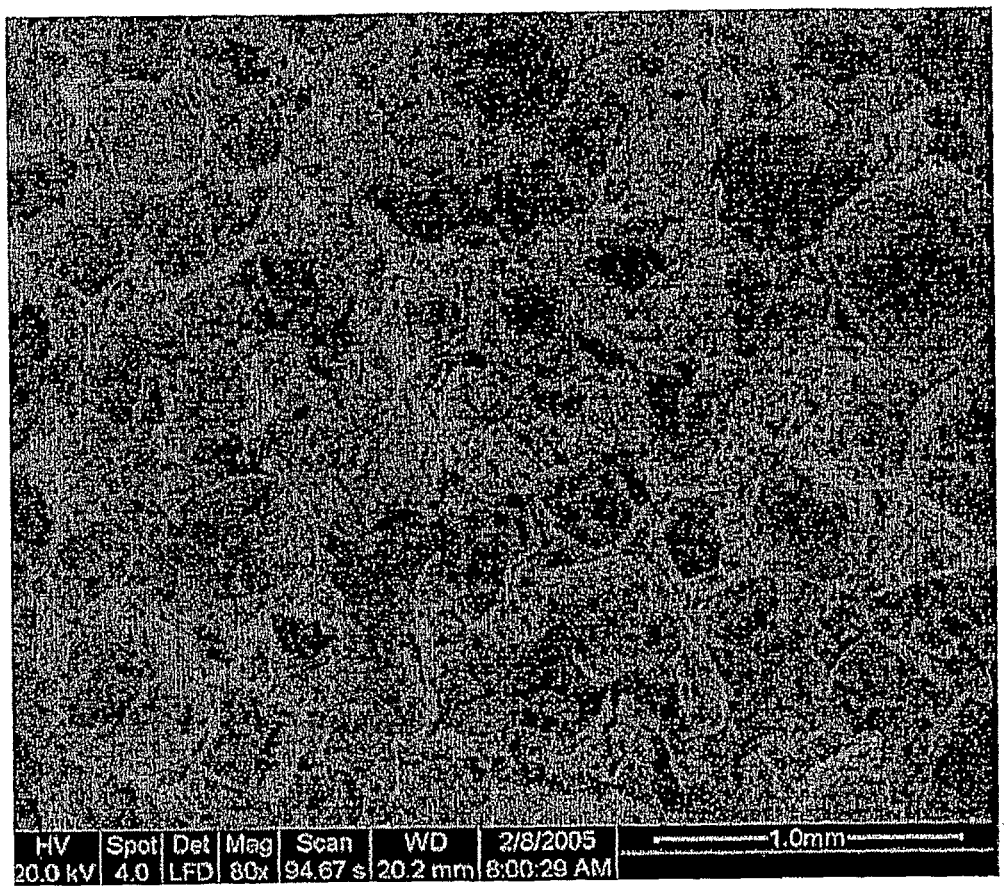
Figure 3:
FIG. 3 is a picture of the morphology of rat neonatal heart fibroplasts on surfaces of a biomedical composition made in accordance with the present disclosure as described further in the examples.

The polymerizing mixture was injected into a mold, allowed to crosslink, and the porogen was leached out by soaking the scaffolds in distilled deionized (DI) water. Pore morphology was investigated with scanning electron microscopy (SEM). Cell behavior on the polymer surfaces was investigated with rat neonatal heart fibroblasts. Hearts were dissected, tissue was minced and digested with collagenase, and fibroblasts were purified by selective attachment to culture dishes. Fibroblasts showed significant adhesion to poly (lactide fumarate) surfaces and the degree of attachment increased by coating the substrates with collagen, laminin, or fabronectin. FIGS. 1 and 2 illustrate the porous scaffold that was fabricated, while FIG. 3 illustrates the morphology of rat neonatal heart fibroblasts on the polymer surfaces.

Example 2

In this example, hydrophilic groups were incorporated into the biodegradable polymer.

In the first step of synthesis, poly(lactide-co-glycolide) blocks were synthesized by melt ring opening polymerization of the lactide and glycolide monomers, as described in Example No. 1. The molar ratio of lactide to diethylene glycol was varied from 10 to 30 to produce low molecular weight polylactide chains with average molecular weights (Mn) in the range of 1000 to 4000 Dalton. The synthesized polymer was characterized by $^1$H-NMR, FTIR, and gel permeation chromatography (GPC). The polydispersity index of the polymer was 1.5-1.6 independent of the polymer molecular weight. The degree of crystallinity of the polymer was also independent of molecular weight in the Mn range of 1000 to 4000 Dalton. The melting point of the semi-crystalline polymer, measured by DSC, depended on the molecular weight of the polymer.

Poly (lactide-co-glycolide fumarate) (PLEOF) was synthesized by condensation polymerization of the above polymer (PLA), poly(ethylene glycol) (PEG), and fumaryl chloride (FuCl) with triethylamine (TEA) as the catalyst. FuCl was purified by distillation at 161° C. and PEG was dried by azeotropic distillation from toluene. The molar ratio of FuCl: PLA+PEG and TEA:PLA+PEG were 0.9:1.0 and 1.8:1.0, respectively. PLEOF macromer was synthesized using PEG with Mn ranging from 1 to 3 kD and PLA with Mn ranging from 1 to 7 kD. The weight ratio of PEG to PLA was varied from 100/0 to 50/50 to produce hydrophilic water-soluble terpolymers.

In a typical reaction, the dried PEG and PLA were dissolved in methylene chloride under dry nitrogen atmosphere in a three-neck reaction flask. The reaction vessel was placed in an ice bath to limit the temperature rise of the exothermic reaction. Next, FuCl and TEA were added to the reaction. After the addition of FuCl and TEA, reaction was continued for 48 h under ambient conditions. After completion of the reaction, solvent was removed and residue was dissolved in anhydrous ethyl acetate. The by-product triethylamine hydrochloride salt was removed by filtration. Ethyl acetate was removed. The macromer was re-dissolved in methylene chloride, precipitated twice in ice cold ethyl ether, and dried before use.

Figure 4:
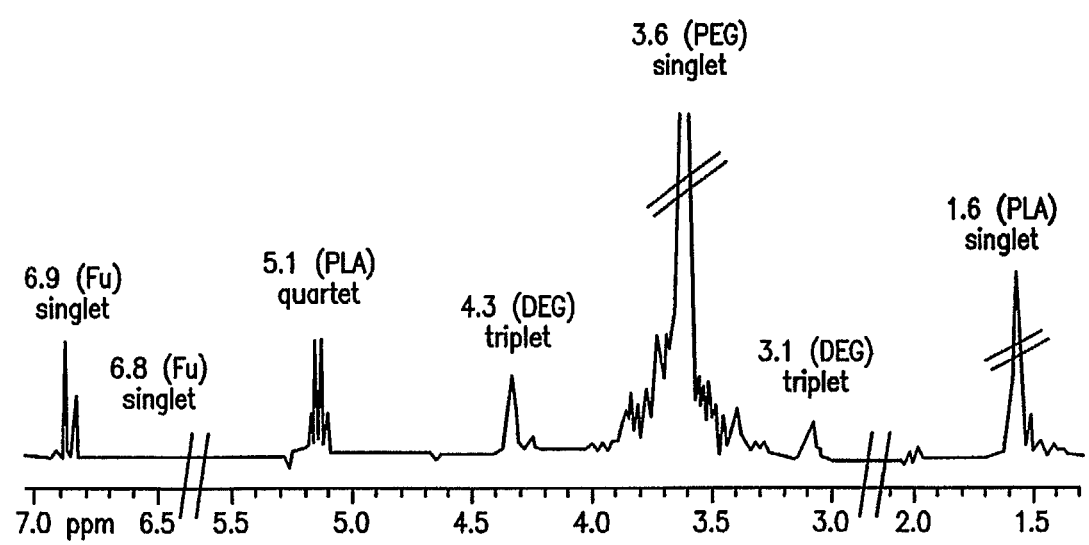
FIG. 4 is an NMR spectrum of a biomedical composition made in accordance with the present disclosure.
Figure 5:
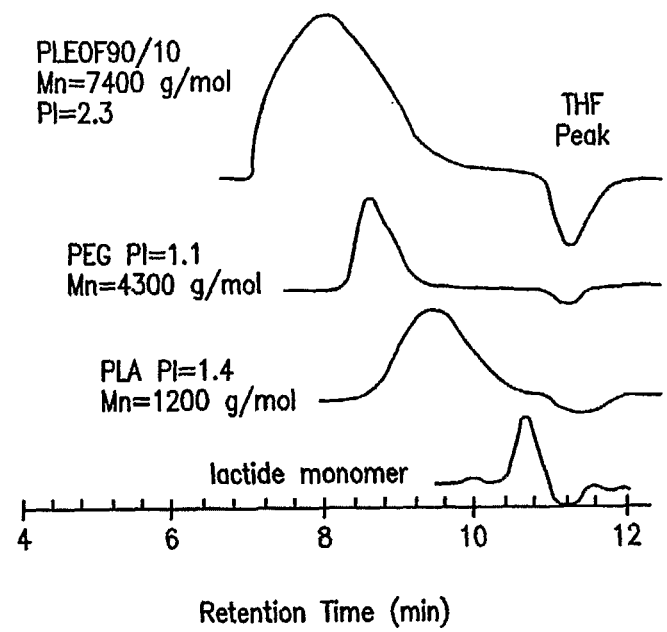
FIG. 5 is a graph illustrating the molecular weights of poly(L-lactide), poly(ethylene oxide) and of a composition made in accordance with the present disclosure.

The structure of the PLEOF macromer was characterized by $^1$H-NMR and FTIR as shown in FIG. 4. Four singlet chemical shifts with peak positions at 1.6, 3.5, 6.8, and 6.9 ppm, two triplets with peaks positions at 3.6 and 4.2 ppm, and a quartet with peak position at 5.1 ppm were observed in $^1$H NMR spectrum of the terpolymer. The presence of peaks at 6.90 ppm in the NMR spectrum, attributable to the hydrogens of the fumarate group, and the presence of a band, due to the ester carbonyl stretching vibration centered at 1725 cm-1 in the FTIR spectrum, confirmed the incorporation of fumarate monomers into the PLEOF macromer. The PLEOF macromer with PLA and PEG molecular weights of 3.3 kD (PI of 1.6) and 3.4 kD (PI of 1.3) had Mn and PI of 6.3 kD and 2.9, respectively, as determined by gel permeation chromatography (GPC). FIG. 5 is a graph illustrating the molecular weights of poly(lactide), polyethylene oxide), lactide monomer, and of a poly(lactide-co-glycolide fumarate) polymer.

Hydrogels were prepared using PLEOF as the degradable macromer, methylenebisacrylamide (MBIS) as the crosslinking agent, and a neutral redox initiation system. The redox system consisted of ammonium persulfate (APS) and tetramethylethylenediamine (TMEDA), respectively.

Figure 6:
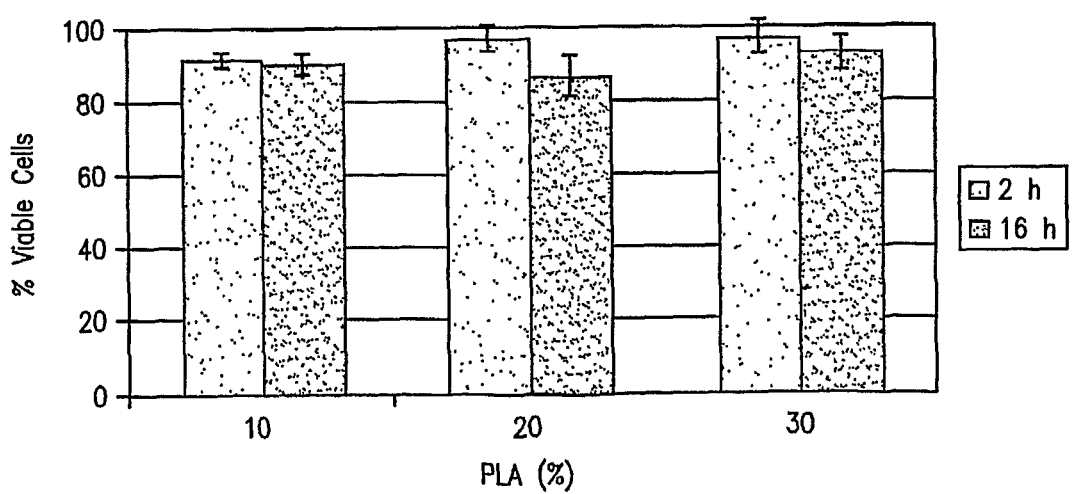
FIG. 6 is a graphical representation of the results obtained in Example No. 2 below.

In a typical procedure, PLEOF was added to 1.65 ml of a 0.24 M solution of BISAM in PBS and vortexed. To this mixture, 0.21 ml of 0.3 M APS and 0.21 ml of 0.3 M TMEDA were added and vortexed. The mixture was degassed, injected between two glass plates separated by a 0.5 mm gap, and fastened with clips. The assembly was placed in a convection oven at 37° C. for 15 minutes to crosslink. After crosslinking, the gel was removed from the glass plate and disks were cut from the gel. The disk-shaped samples were used for swelling and cell viability studies. The results of the cell viability study are illustrated in FIG. 6. The water content, mesh size, and degradation characteristics of these novel terpolymer hydrogels can be controlled independently by the molecular weight of PEG, the weight ratio of PLA to PEG, and the molecular weight of PLA, respectively.

Example 3

In this example, a composite biodegradable polymer was produced in accordance with the present disclosure.

PLEOF Synthesis

Low molecular weight poly(lactic acid) (LMW PLA) was synthesized by ring opening polymerization of the lactide monomer (LA) in a dry atmosphere with diethylene glycol (DEG) as the bifunctional initiator and tin octoate (TOC) as the polymerization catalyst. The molar ratio of DEG to TOC was 25:1. The molar ratio of LA to DEG was varied from 10 to 30 to produce LMW PLA with average molecular weights (Mn) in the range of 1000 to 4000 Dalton. The synthesized LMW PLA was characterized by $^1$H NMR and gel permeation chromatography (GPC). PLEOF was synthesized by condensation polymerization of LMW PLA and poly(ethylene glycol) (PEG) with fumaryl chloride (FuCl) and triethylamine (TEA) as the catalyst. The molar ratio of FuCl:PEG and TEA:PEG was 0.9:1.0 and 1.8:1.0, respectively. PLEOF terpolymer was synthesized using PEG with Mn ranging from 1 to 4.5 kD and LMW PLA with Mn ranging from 1 to 4 kD. The weight ratio of PEG to PLA was varied from 100/0 to 70/30 to produce hydrophilic water-soluble terpolymers. The structure of PLEOF macromer was characterized by $^1$H-NMR and FTIR.

Synthesis of Peptide Crosslinker

MMP degradable lysine-alanine-isoleucine-glycine-glutamine-histidine-lysine amino acid sequence with unsaturated reactive end groups, hereafter designated as the peptide crosslinker, was synthesized manually in the solid phase using a method on the Rink Amide NovaGel™ resin with Fmoc-, Mtt-, and Trt- protected amino acid derivatives. After coupling the last amino acid of the peptide chain, the Mtt protecting group was selectively deprotected by treating the peptidyl resin with trifluoroacetic acid/dichloromethane (TFA/DCM) (1:99 v/v) and filtered. The resin was washed and the Fmoc amino acids were deprotected by treatment with 20% piperidine in DMF. Bifunctional peptide with unsaturated acrylate end groups was synthesized in the solid phase by coupling acrylic acid to the amine groups of glutamine and lysine residues at the two ends of the peptide sequence. The product was purified by preparative HPLC at a flow rate 2 ml/min using a gradient 5% acetonitrile (MeCN) and 95% 0.1% aqueous TFA solvent mixture. A photodiode array detector was used for detection at a wavelength of 214 nm. Mass spectrometric (MS) studies were performed with a Fannigan 4500 Electro Spray Ionization (ESI) spectrometer.

Scaffold Fabrication and Cell Biocompatibility

Solid or porous hydrogel/apatite scaffolds were prepared using PLEOF as the degradable macromer, methylene bisacrylamide (MBIS) or MMP degradable unsaturated peptide as the crosslinking agents, and a neutral redox initiation system. Sodium chloride (NaCl) crystals were used as the porogen in fabrication of porous scaffolds. The redox system consisted of APS and TMEDA, respectively. The pore morphology was studied with an ESEM FEI XL30 equipped with an electron backscattered detector and an integrated EDAX system. Cell attachment on the PLEOF hydrogel/apatite nanocomposite surface was investigated with rat neonatal heart fibroblasts.

For isolation of neonatal heart fibroblasts, rats were sacrificed by decapitation 2-3 days after birth. Hearts were dissected free of extra-cardiac tissue. Heart tissue was minced and digested with collagenase. Fibroblasts were purified and maintained in DMEM containing 10% fetal bovine serum (FBS), 5% neonatal calf serum and antibiotics. Disk-shaped samples 6×1 mm were sterilized with ethanol and added to each well of a 12 well plate coated with fibrinogen (to make the surface non-adherent to cells) at a density of 1×10⁴ cells/cm². The plate was incubated for 48 hours for cell attachment. The disks were permeabilized by soaking in PBS with 0.1% triton ×100 and 0.1M glycine. Cell nucleus was stained with SYTOX Green (1:5000 dilution) and the cytoplasm was counterstained with Texas Red-X Phalloidin (1:1000 dilution).

Figure 7:
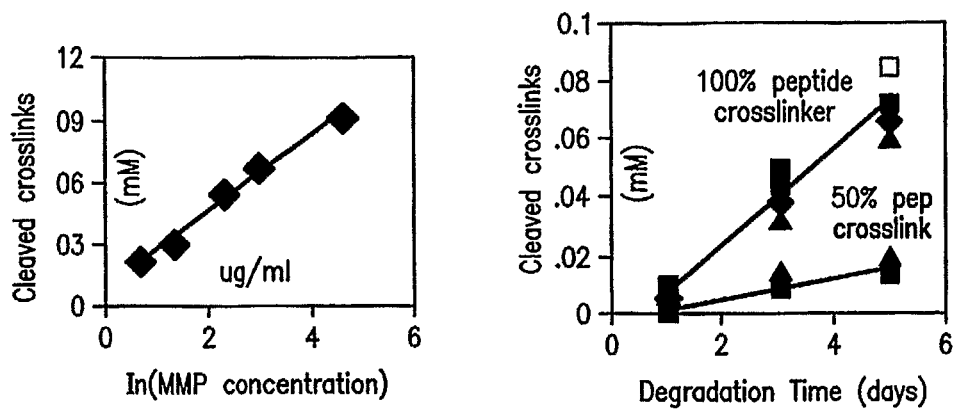

The results of a degradation study on the biodegradable polymer are shown in FIG. 7.

Example 4

In the following example, poly(lactide-ethylene oxide-fumarate) terpolymers ("PLEOF") comprised of short lactide and ethylene oxide chains linked by unsaturated fumarate units were synthesized. The swelling and degradation characteristics of the PLEOF terpolymer were investigated.

Difunctional hydroxyl terminated short lactide chains were first synthesized by melt ring-opening polymerization of L-lactide (LA) monomer with diethylene glycol (DEG) as the initiator and tin II-ethyl hexanoate as the catalyst. The molar ratio of LA to DEG was varied from 10 to 30 to produce low molecular weight PLA (LMWPLA) chains with number average molecular weights (Mn) in the range of 1000 to 4000 Dalton. The synthesized LMWPLA was characterized by $^1$H-NMR, FTIR, and gel permeation chromatography (GPC). The polydispersity index of PLA was 1.5-1.6 independent of the PLA molecular weight. The degree of crystallinity of PLA was also independent of PLA molecular weight in the Mn range of 1000 to 4000 Dalton. The melting point of the semi-crystalline PLA, measured by DSC, depended on the molecular weight of the LMW PLA.

PLEOF was synthesized by condensation polymerization of low MW PLA, poly(ethylene glycol) (PEG), and fumaryl chloride (FuCl) with triethylamine (TEA) as the catalyst. FuCl was purified by distillation at 161° C. and PEG was dried by azeotropic distillation from toluene. The molar ratio of FuCl:PLA+PEG and TEA:PLA+PEG were 0.9:1.0 and 1.8:1.0, respectively. PLEOF macromer was synthesized using PEG with Mn ranging from 1 to 5 kD and PLA with Mn ranging from 1 to 7 kD. The weight ratio of PEG to PLA was varied from 100/0 to 85/15 to produce hydrophilic water-soluble terpolymers.

In a typical reaction, the dried PEG and LMW PLA were dissolved in methylene chloride under dry nitrogen atmosphere in a three-neck reaction flask. The reaction vessel was placed in an ice bath to limit the temperature rise of the exothermic reaction. Next, FC and TEA each dissolved were added dropwise to the reaction with stirring. After the addition of FC and TEA, reaction was continued for 6 h under ambient conditions. After completion of the reaction, solvent was removed by and residue was dissolved in anhydrous ethyl acetate. The mixture was kept at 5° C. for 12 h for complete precipitation of the by-product triethylamine hydrochloride and the salt was removed by filtration. Ethyl acetate was removed by vacuum distillation at 30° C. The macromer was re-dissolved in methylene chloride, precipitated twice in ice cold ethyl ether, and dried before use.

The structure of PLEOF macromer was characterized by $^1$H-NMR and FTIR. The presence of peaks at 6.90 ppm in the NMR spectrum attributable to hydrogens of the fumarate group, and presence of a band due to the ester carbonyl stretching vibration centered at 1725 cm$^{-1}$ in the FTIR spectra, confirmed the incorporation of fumarate monomers into the PLEOF macromer. The ratio of the peaks in the NMR spectrum of PLEOF due to chemical shifts centered at 5.1 ppm (due to the one hydrogen attached to the methine group of the lactide monomer) and 3.6 ppm (due to the four methylene hydrogens (CH2-CH2-O—) of ethylene oxide repeat units) was related to the molar ratio of the PLA to PEG in the terpolymer. For 10% by weight PLA in the feed, this ratio was 0.055, corresponding to 5.2% by mole and 8.7% by weight of the PLA in the terpolymer. Therefore, the copolymer reactivity of PLA with fumaryl chloride was slightly less than that of PEG.

The PLEOF macromer with PLA and PEG molecular weights of 3.3 kD (PI of 1.6) and 3.4 kD (PI of 1.3) had Mn and PI of 6.3 kD and 2.9, respectively, as determined by gel permeation chromatography (GPC).

Figure 8:
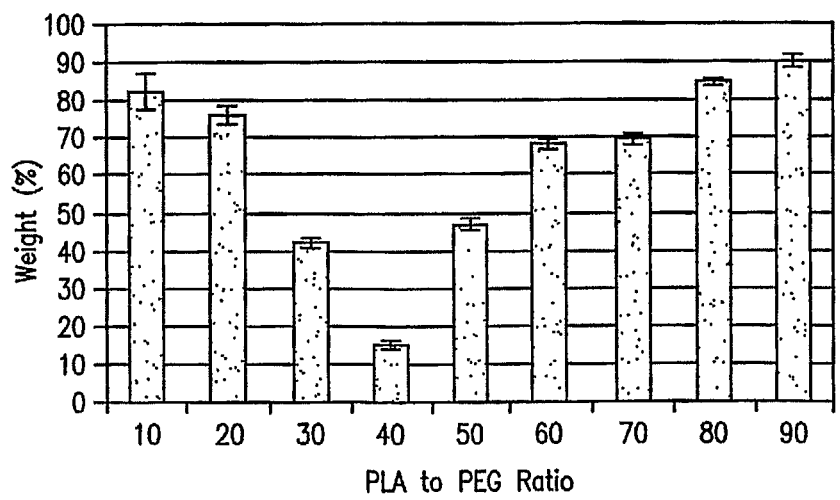
FIG. 8 is a graphical representation of data obtained in Example 4 below.

Polymers were prepared using PLEOF as the degradable macromer, methylenebisacrylamide (MBIS) as the crosslinking agent, and a neutral redox initiation system. The redox system consisted of ammonium persulfate (APS) and tetramethylethylenediamine (TMEDA), respectively. The disk-shaped samples were used for swelling, cell viability, cell function, and degradation studies (see FIG. 8).

The results demonstrate that the water content, mesh size, and degradation characteristics of these terpolymers can be controlled independently by the molecular weight of PEG, the weight ratio of PLA to PEG, and the molecular weight of PLA, respectively. For example, the weight swelling ratio in water ranged from 0.1 to 6 for PLA:PEG ratios of 0.1 to 0.9, respectively. When the PLA content was increased from 10 to 20, 30, 40, 50, 60, 70, 80, and 90%, the weight loss after 21 days changed from 17 to 24, 58, 85, 53, 32, 31, 15, and 10%, respectively.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A bioresorbable composite composition comprising:
a biodegradable hydrogel polymer crosslinked to ceramic particles, the biodegradable hydrogel polymer comprising a poly(lactide-co-glycolide) block, a poly(ethylene oxide) block, and a fumarate group, the fumarate group comprising reactive groups for crosslinking the biodegradable hydrogel polymer, the biodegradable hydrogel polymer being formed by reaction of a poly(lactide-co-glycolide) polymer having a number average molecular weight of greater than 500 Daltons and less than 8,000 Daltons with a poly(ethylene oxide) compound having a number average molecular weight of from 500 Daltons to 5,000 Daltons and with a fumaryl compound, the biodegradable hydrogel polymer having a number average molecular weight of less than 15,000 Daltons and having a polydispersity index of less than 3.5, wherein the molar ratio of the polylactide-co-glycolide) polymer to the fumaryl compound is from 1:0.8 to 1:0.99, the biodegradable hydrogen polymer being crosslinked to the ceramic particles by a crosslinking agent that comprises a peptide crosslinking agent or that comprises methylene bis acrylamide.

2. The bioresorbable composite composition as defined in claim 1, wherein the ceramic particles comprise calcium phosphate particles.

3. The bioresorbable composite composition as defined in claim 1, wherein the ceramic particles comprise apatite particles.

4. The bioresorbable composite composition as defined in claim 1, wherein the ceramic particles comprise tricalcium phosphate particles.

5. The bioresorbable composite composition as defined in claim 2, wherein the ceramic particles have an average particle size of less than about 1 micron.

6. The bioresorbable composite composition of claim 1, wherein the fumaryl compound comprises fumaryl chloride.

7. The bioresorbable composite composition of claim 1, wherein the composition further comprises a porogen.

8. The bioresorbable composite hydrogel composition of claim 1, wherein the weight ratio of the polyethylene oxide) compound to the poly(lactide-co-glycolide) polymer is from about 99:1 to about 85:15.

9. The bioresorbable composite composition as defined in claim 1, wherein the peptide crosslinking agent is metalloproteinase degradable.

10. A biomedical product for repairing skeletal tissue comprising:
a first container comprising the biodegradable hydrogel polymer as defined in claim 1 combined with the ceramic particles; and
a second container comprising the crosslinking agent.

11. The biomedical product as defined in claim 10, wherein at least the first container or the second container further comprises an initiator, the initiator comprising a reducing agent and an oxidizing agent.

12. The biomedical product of claim 11, wherein at least the first container or the second container further comprises an accelerator.

13. A method of repairing skeletal tissue comprising:
forming the bioresorbable composite composition of claim 1 by combining the crosslinking agent and the ceramic particles with the biodegradable hydrogel polymer; and
applying the biomedical composition to a prepared area of a patient's body, the biomedical composition being applied to skeletal tissue for repairing the tissue, the biomedical composition biodegrading over a period of time.

* * * * *